(12) United States Patent
Urihara

(10) Patent No.: US 9,034,835 B2
(45) Date of Patent: May 19, 2015

(54) PLANT DISEASE CONTROL AGENT WITH A TETRAZOLYL OXIME DERIVATIVE AND EITHER TRIFLUMIZOLE OR HYDROXY-ISOXAZOLE AS THE ACTIVE INGREDIENTS

(75) Inventor: Ichirou Urihara, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/583,740

(22) PCT Filed: Mar. 14, 2011

(86) PCT No.: PCT/JP2011/055879
§ 371 (c)(1),
(2), (4) Date: Sep. 10, 2012

(87) PCT Pub. No.: WO2011/115029
PCT Pub. Date: Sep. 22, 2011

(65) Prior Publication Data
US 2013/0005672 A1  Jan. 3, 2013

(30) Foreign Application Priority Data
Mar. 16, 2010 (JP) .................. 2010-059638

(51) Int. Cl.
| | |
|---|---|
| C07D 401/12 | (2006.01) |
| A01N 43/50 | (2006.01) |
| A01N 43/80 | (2006.01) |
| A01N 43/713 | (2006.01) |
| C07D 233/56 | (2006.01) |
| C07D 261/12 | (2006.01) |

(52) U.S. Cl.
CPC .............. *C07D 401/12* (2013.01); *A01N 43/50* (2013.01); *A01N 43/80* (2013.01); *C07D 233/56* (2013.01); *C07D 261/12* (2013.01); *A01N 43/713* (2013.01)

(58) Field of Classification Search
None
See application file for complete search history.

(56) References Cited

U.S. PATENT DOCUMENTS

| | | | | |
|---|---|---|---|---|
| 3,687,968 | A * | 8/1972 | Iwai et al. ................ | 548/243 |
| 8,592,412 | B1 * | 11/2013 | Urihara et al. ............ | 514/229.2 |
| 8,592,461 | B2 * | 11/2013 | Urihara et al. ............ | 424/632 |
| 2011/0052555 | A1 * | 3/2011 | Coqueron et al. ........ | 424/93.461 |
| 2011/0287108 | A1 * | 11/2011 | Coqueron et al. ........ | 424/605 |
| 2012/0027741 | A1 * | 2/2012 | Coqueron et al. ........ | 424/93.461 |
| 2012/0309972 | A1 * | 12/2012 | Ito et al. ................... | 546/15 |

FOREIGN PATENT DOCUMENTS

| | | | |
|---|---|---|---|
| JP | 2007-008891 A | 1/2007 | |
| JP | 2007-161621 A | 6/2007 | |
| WO | WO 03/016303 A1 | 2/2003 | |
| WO | WO 2009/020191 A1 | 2/2009 | |
| WO | WO 2009020191 A1 * | 2/2009 | ........... C07D 401/12 |
| WO | WO 2009/090181 A2 | 7/2009 | |
| WO | WO 2009090181 A2 * | 7/2009 | |
| WO | WO 2009/119072 A1 | 10/2009 | |
| WO | WO 2010/060982 A2 | 6/2010 | |

OTHER PUBLICATIONS

Kobori et al., WO 2009020191 A1, Feb. 2009, machine translation. Retreived on Nov. 8, 2013 from http://worldwide.espacenet.com.*
Casida, J. E. (2009). Pest toxicology: the primary mechanisms of pesticide action. Chemical research in toxicology, 22(4), 609-619.*
Nauen, R., Ebbinghaus-Kintscher, U., Salgado, V. L., & Kaussmann, M. (2003). Thiamethoxam is a neonicotinoid precursor converted to clothianidin in insects and plants. Pesticide Biochemistry and Physiology, 76(2), 55-69.*
Inam, R., Gülerman, E. Z., & Sarigül, T. (2006). Determination of triflumizole by differential pulse polarography in formulation, soil and natural water samples. Analytica chimica acta, 579(1), 117-123.*
Cisneros, J., Goulson, D., Derwent, L. C., Penagos, D. I., Hernández, O., & Williams, T. (2002). Toxic effects of spinosad on predatory insects. Biological Control, 23(2), 156-163.*
Veneziano, A., Vacca, G., Arana, S., De Simone, F., & Rastrelli, L. (2004). Determination of carbendazim, thiabendazole and thiophanate-methyl in banana (<i>Musa acuminata</i>) samples imported to Italy. Food chemistry, 87(3), 383-386.*
Kurahashi, Y. (2001). Melanin biosynthesis inhibitors (MBIs) for control of rice blast. Pesticide Outlook, 12(1), 32-35.*
Horowitz, A. R., Mendelson, Z., Weintraub, P. G., & Ishaaya, I. (1998). Comparative toxicity of foliar and systemic applications of acetamiprid and imidacloprid against the cotton whitefly, *Bemisia tabaci* (Hemiptera: Aleyrodidae). Bulletin of entomological research, 88(04), 437-442.*
Japanese Office Action dated Jan. 7, 2014, in JP 2012-505654 with English translation.

* cited by examiner

*Primary Examiner* — Shaojia Anna Jiang
*Assistant Examiner* — Dale R Miller
(74) *Attorney, Agent, or Firm* — Foley & Lardner LLP

(57) ABSTRACT

According to the present invention, a plant disease control agent having a superior control effect on plant diseases at a low dose is provided. The plant disease control agent of the present invention includes at least one selected from tetrazolyl oxime derivatives represented by formula (I) and salts thereof, and at least one selected from the group consisting of imidacloprid, triflumizole, spinosad, hydroxy isoxazole, thiophanate-methyl, tricyclazole, clothianidin, benomyl, acetamiprid and salts thereof. In formula (I), X represents a C1-6 alkyl group or the like; n represents an integer of 0 to 5; Y represents a C1-6 alkyl group; Z represents a group represented by NHC(=O)-Q; Q represents a C1-8 alkoxy group or the like; R represents a halogen atom; m represents an integer of 0 to 3.

5 Claims, No Drawings

PLANT DISEASE CONTROL AGENT WITH A TETRAZOLYL OXIME DERIVATIVE AND EITHER TRIFLUMIZOLE OR HYDROXY-ISOXAZOLE AS THE ACTIVE INGREDIENTS

TECHNICAL FIELD

The present invention relates to a plant disease control agent including as an effective ingredient tetrazolyl oxime derivatives and fungicidal active ingredients for agricultural and horticultural use.

Priority is claimed on Japanese Patent Application No. 2010-059638, filed Mar. 16, 2010, the content of which is incorporated herein by reference.

BACKGROUND ART

In the cultivation of agricultural and horticultural crops, although a large number of disease control agents are used against crop disease, most of them are not necessarily considered to be satisfactory, since the control effects thereof may be inadequate, or the use thereof may be restricted due to the appearance of agrichemical-resistant pathogenic organisms, or the plants may be damaged or contaminated by agrichemicals, or the agrichemical may demonstrate toxicity to humans, livestock or marine life. Thus, there is a need to develop a plant disease control agent that can be used safely and has few of these shortcomings.

The present inventors carried out exhaustive research in view of the above-described circumstances, and discovered that a tetrazolyl oxime derivative and/or salt thereof are useful as an active ingredient of a plant disease control agent, and previously filed a patent application (Patent document 1).

PRIOR ART LITERATURE

Patent Documents

Patent document 1: WO 03/016303

DISCLOSURE OF INVENTION

Problems to be Solved by the Invention

The present invention was carried out as a part of research on a plant disease control agent including a tetrazolyl oxime derivative and/or salt thereof described in Patent document 1 as an active ingredient, and an objective of the present invention is to provide a plant disease control agent that provides excellent control effects against plant disease at low doses.

Means for Solving the Problems

In order to solve the aforementioned objective, the inventors of the present invention carried out further research on a plant disease control agent including tetrazolyl oxime derivative and/or salt thereof described in Patent document 1 as an active ingredient. As a result, the inventors of the present invention discovered that superior control effects against plant disease at low doses can be obtained by using the said tetrazolyl oxime derivative and/or salt thereof together with a fungicidal active ingredient for agricultural and horticultural use, and completed the present invention.

Thus, the present invention provides a plant disease control agent including at least one selected from tetrazolyl oxime derivatives represented by formula (I) and salts thereof

[Chemical formula 1]

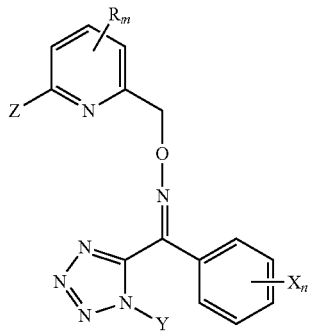

(in formula (I), X represents a C1-6 alkyl group, C1-6 alkoxy group, halogen atom, nitro group, cyano group, C6-10 aryl group, or C1-6 alkyl sulfonyl group; n represents an integer of 0 to 5; Y represents a C1-6 alkyl group; Z represents a hydrogen atom, amino group, or a group represented by NHC(=O)-Q; Q represents a hydrogen atom, C1-8 alkyl group, C1-6 haloalkyl group, C3-6 cycloalkyl group, C1-8 alkoxy group, C3-6 cycloalkyloxy group, C7-20 aralkyloxy group, C1-4 alkyl thio C1-8 alkyl group, C1-4 alkoxy C1-2 alkyl group, C1-4 acyl amino C1-6 alkyl group, C1-4 acyl amino C1-6 alkoxy group, C1-8 alkyl amino group, C2-6 alkenyl group, C7-20 aralkyl group or C6-10 aryl group; R represents a halogen atom; m represents an integer of 0 to 3) and at least one selected from the group consisting of imidacloprid, triflumizole, spinosad, hydroxy isoxazole, thiophanate-methyl, tricyclazole, clothianidin, benomyl, acetamiprid and salts thereof.

Effects of the Invention

The plant disease control agent of the present invention provides excellent control effects against plant disease at low doses, and eliminates concern over chemical damage to useful plants.

BEST MODE FOR CARRYING OUT THE INVENTION

The plant disease control agent of the present invention includes at least one selected from tetrazolyl oxime derivatives represented by formula (I) and salts thereof, and at least one selected from specific fungicidal active ingredients for agricultural and horticultural use.

(1) Tetrazolyl Oxime Derivative and Salt Thereof

[X]

In formula (I), X represents a C1-6 alkyl group, C1-6 alkoxy group, halogen atom, nitro group, cyano group, C6-10 aryl group, or C1-6 alkyl sulfonyl group.

Examples of the C1-6 alkyl group of X include a methyl group, ethyl group, n-propyl group, i-propyl group, n-butyl group, s-butyl group, i-butyl group, t-butyl group, n-pentyl group, n-hexyl group and the like.

Examples of the C1-6 alkoxy group of X include a methoxy group, ethoxy group, n-propoxy group, i-propoxy group, n-butoxy group, s-butoxy group, i-butoxy group, t-butoxy group and the like.

The C1-6 alkyl group or C1-6 alkoxy group may be substituted. The substituents are not particularly limited as long as they are chemically permissible. Examples of the substituents include a halogen atom such as a fluorine atom, chlorine atom, bromine atom, iodine atom or the like; a C1-6 alkoxy group such as a methoxy group, ethoxy group, n-propoxy group, i-propoxy group, n-butoxy group, s-butoxy group, i-butoxy group, t-butoxy group or the like; an unsubstituted or substituted phenyl group such as a phenyl group, 4-methyl phenyl group, 2-chlorophenyl group or the like; a nitro group; a cyano group; an unsubstituted or substituted amino group such as an amino group, methyl amino group, dimethyl amino group, acetyl amino group, benzoyl amino group or the like; and the like.

Examples of the halogen atom of X include a fluorine atom, chlorine atom, bromine atom, iodine atom and the like.

Examples of the C6-10 aryl group of X include a phenyl group, 1-naphthyl group, 2-naphthyl group and the like.

The aryl group may be substituted. The substituents are not particularly limited as long as they are chemically permissible. Examples of the substituents include a halogen atom such as a fluorine atom, chlorine atom, bromine atom, iodine atom or the like; a C1-6 alkyl group such as a methyl group, ethyl group, n-propyl group, i-propyl group, n-butyl group, s-butyl group, i-butyl group, t-butyl group, n-pentyl group, n-hexyl group or the like; a C2-6 alkenyl group such as a vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group or the like; a C2-6 alkynyl group such as an ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group or the like; a C1-6 alkoxy group such as a methoxy group, ethoxy group, n-propoxy group, i-propoxy group, n-butoxy group, s-butoxy group, i-butoxy group, t-butoxy group or the like; a nitro group; a cyano group; and the like.

Examples of the C1-6 alkyl sulfonyl group of X include a methyl sulfonyl group, ethyl sulfonyl group, n-propyl sulfonyl group, i-propyl sulfonyl group and the like.

The C1-6 alkyl sulfonyl group may be substituted. The substituents are not particularly limited as long as they are chemically permissible. Examples of the substituents are the same as those listed as examples of the substituents of the C1-6 alkyl group of X.

Among those examples, X preferably represents a halogen atom. n represents an integer of 0 to 5, and preferably represents 0.

[Y]

In formula (I), Y represents a C1-6 alkyl group.

Examples of the C1-6 alkyl group of Y are the same as those listed as examples of the C1-6 alkyl group of X.

Among those examples, Y preferably represents a methyl group.

[Z]

In formula (I), Z represents a hydrogen atom, amino group, or a group represented by NHC(=O)-Q;

Q represents a hydrogen atom, C1-8 alkyl group, C1-6 haloalkyl group, C3-6 cycloalkyl group, C1-8 alkoxy group, C3-6 cycloalkyloxy group, C7-20 aralkyloxy group, C1-4 alkyl thio C1-8 alkyl group, C1-4 alkoxy C1-2 alkyl group, C1-4 acyl amino C1-6 alkyl group, C1-4 acyl amino C1-6 alkoxy group, C1-8 alkyl amino group, C2-6 alkenyl group, C7-20 aralkyl group or C6-10 aryl group.

Examples of the C1-8 alkyl group of Q include a methyl group, ethyl group, n-propyl group, i-propyl group, 1,1-dimethyl propyl group, n-butyl group, i-butyl group, s-butyl group, t-butyl group, 1-methyl butyl group, 2-methyl butyl group, neopentyl group, 1-ethyl propyl group, n-pentyl group, n-hexyl group, n-heptyl group, n-octyl group and the like.

Examples of the C1-6 haloalkyl group of Q include a chloromethyl group, difluoromethyl group, trifluoromethyl group, difluorochloromethyl group, pentafluoroethyl group, 3,3,3-trifluoro-n-propyl group, 1-chlorohexyl group and the like.

Examples of the C3-6 cycloalkyl group of Q include a cyclopropyl group, cyclobutyl group, cyclopentyl group, cyclohexyl group and the like.

Examples of the C1-8 alkoxy group of Q include a methoxy group, ethoxy group, propoxy group, i-propoxy group, 1,1-dimethyl-n-propoxy group, n-butoxy group, i-butoxy group, s-butoxy group, t-butoxy group, i-pentyloxy group, 1-methyl butoxy group, 2-methyl butoxy group, neopentyloxy group, 1-ethyl propoxy group, n-pentyloxy group, n-hexyloxy group, n-heptyloxy group, n-octyloxy group and the like Examples of the C3-6 cycloalkyloxy group of Q include a cyclopropyloxy group, cyclobutyloxy group, cyclopentyloxy group, cyclohexyloxy group and the like.

Examples of the C7-20 aralkyloxy group of Q include a benzyloxy group, phenethyloxy group and the like.

Examples of the C1-4 alkyl thio C1-8 alkyl group of Q include a methyl thiomethyl group, 2-methyl thioethyl group, ethyl thiomethyl group, butyl thiomethyl group and the like.

Examples of the C1-4 alkoxy C1-2 alkyl group of Q include a methoxymethyl group, ethoxymethyl group, 2-methoxyethyl group, 2-ethoxyethyl group, n-butoxymethyl group and the like.

Examples of the C1-4 acyl amino C1-6 alkyl group of Q include an acetyl aminomethyl group, 2-(propionyl amino) ethyl group, 3-(acetyl amino)propyl group, 3-(propionyl amino)propyl group, 3-(pivaloyl amino)propyl group, 4-(acetyl amino)butyl group, 5-(acetyl amino)pentyl group, 6-(acetyl amino)hexyl group and the like.

Examples of the C1-4 acyl amino C1-6 alkoxy group of Q include an acetyl aminomethoxy group, 2-(propionyl amino) ethoxy group, 3-(acetyl amino)propoxy group, 3-(propionyl amino)propoxy group, 3-(pivaloyl amino)propoxy group and the like.

Examples of the C1-8 alkyl amino group of Q include a methyl amino group, ethyl amino group, n-propyl amino group, i-propyl amino group, n-butyl amino group, i-butyl amino group, s-butyl amino group, t-butyl amino group, neopentyl amino group, 1-ethyl propyl amino group, n-pentyl amino group, n-hexyl amino group, n-heptyl amino group, n-octyl amino group and the like.

Examples of the C2-6 alkenyl group of Q include an allyl group, i-propenyl group, 1-butenyl group, 2-butenyl group, 2-pentenyl group, 5-hexenyl group and the like.

Examples of the C7-20 aralkyl group of Q include a benzyl group, phenethyl group, 3-phenyl propyl group, 1-naphthyl methyl group, 2-naphthyl methyl group and the like.

Examples of the C6-10 aryl group of Q include a phenyl group, 1-naphthyl group, 2-naphthyl group and the like.

Among those examples, Z preferably represents a group represented by NHC(=O)-Q, or a group represented by NHC(=O)—O-t-Bu. In addition, t-Bu represents tertiary butyl group.

[R]

In formula (I), R represents a halogen atom such as a fluorine atom, chlorine atom, bromine atom or the like. m represents an integer of 0 to 3, and preferably represents 0.

Salts of the tetrazolyl oxime derivative represented by formula (I) are not particularly limited as long as they are agriculturally and horticulturally acceptable. Examples of the salts include a salt of inorganic acids such as hydrochlorides, nitrates, sulfates or phosphates; a salt of organic acids such as acetates, lactates, propionates or benzoates; and the like.

(E)-form and (Z)-form stereoisomers exist in the tetrazolyl oxime derivative represented by the aforementioned formula (I) based on carbon-nitrogen double bonds. These two stereoisomers along with mixtures thereof are also included in the present invention. Synthetic products are normally obtained in the form of the (Z)-form only or as a mixture of the (E)-form and (Z)-form. The two isomers can be respectively isolated from a mixture of the (E)-form and (Z)-form by separating in accordance with known techniques such as silica gel column chromatography.

The (Z)-form of the tetrazolyl oxime derivative represented by formula (I) used in the present invention, and salts thereof, has superior plant disease control effects as compared with the (E)-form. However, since the (Z)-form is partially converted to the (E)-form due to the action of light and the like in the natural environment, and tends to stabilize at a constant ratio in the form of a mixture of the (E)-form and the (Z)-form, both of these compounds as well as mixtures thereof are useful. Furthermore, since the stable ratio of the (E)-form to the (Z)-form varies according to individual compounds, it cannot be universally specified.

The tetrazolyl oxime derivative represented by formula (I) and salt thereof may be produced, for example, by a method described in WO 03/016303.

Examples of the tetrazolyl oxime derivative represented by formula (I) include the compounds described in WO03/016303.

(2) Fungicidal Active Ingredient for Agricultural and Horticultural Use

In addition to the above-described tetrazolyl oxime derivative and salt thereof (hereafter, may be referred to as "tetrazolyl oxime derivative or the like"), the plant disease control agent of the present invention further includes at least one selected from the group consisting of imidacloprid, triflumizole, spinosad, hydroxy isoxazole, thiophanate-methyl, tricyclazole, clothianidin, benomyl, acetamiprid and salts thereof These compounds are well-known fungicidal active ingredients for agricultural and horticultural use. For example, Admire flowable (active ingredient: 20% of imidacloprid, manufactured by Bayer Holding Ltd.), Trifmine wettable powder (active ingredient: 30% of triflumizol, manufactured by Dow Chemical Japan Ltd.), Spinoace wettable granule (active ingredient: 25% of spinosad, manufactured by Dow Chemical Japan Ltd.), Tachigaren liquid formulation (active ingredient: 30% of hydroxyisoxazol, manufactured by Sankyo Agro Co., Ltd.), Topsin M wettable powder (active ingredient: 70% of thiophanate-methyl, manufactured by Nippon Soda Co., Ltd), Beam Sol (active ingredient: 20% of tricyclazoyl, manufactured by Sumitomo Chemical Company, Limited), Dantotsu water-soluble powder (active ingredient: 16% of clothiazine, manufactured by Sumitomo Chemical Company), Benreto wettable powder (active ingredient: 50% of benolyl, manufactured by Sumitomo Chemical Company), Mospiran SL liquid formulation (active ingredient: 18% of acetamiprid, manufactured by Nippon Soda Co., Ltd.) are commercially available.

In the plant disease control agent of the present invention, the composition ratio between (1) tetrazolyl oxime derivative or the like and (2) the fungicidal active ingredient for agricultural and horticultural use is not particularly limited. The ratio by weight of (tetrazolyl oxime derivative or the like):(fungicidal active ingredient for agricultural and horticultural use) is preferably 1:10,000,000 to 10,000,000:1, more preferably 1:1,000,000 to 1,000,000:1, more preferably 1:100,000 to 100,000:1, particularly preferably 1:10,000 to 10,000:1.

In the plant disease control agent, the content rate of the total amount of (1) the tetrazolyl oxime derivative or the like and (2) the active ingredient for agricultural and horticultural use is not particularly limited, and can be varied according to formulation. For example, in wettable powders, the content rate is normally 5 to 90% by weight, preferably 10 to 85% by weight; in emulsions, the content rate is normally 3 to 70% by weight, preferably 5 to 60% by weight; in granules, the concentrate is normally 0.01 to 50% by weight, preferably 0.05 to 40% by weight.

(3) Other Components

In the plant disease control agent of the present invention, additive agents such as rape oil, soybean oil, sunflower seed oil, castor oil, pine oil, cotton seed oil or derivatives thereof, or oil concentrates thereof may be added.

In addition, the plant disease control agent of the present invention may further include a pesticide active ingredient such as insecticides, miticides, herbicides, plant growth regulators, fertilizers or the like according to need.

Formulation of the plant disease control agent of the present invention is not particularly limited as long as the plant disease control agent includes (1) the tetrazolyl oxime derivative or the like, and (2) the fungicidal active ingredient for agricultural and horticultural use.

Examples of the plant disease control agent include a plant disease control agent obtained by mixing (1) a formulation including the tetrazolyl oxime derivative or the like, (2) a formulation including the fungicidal active ingredient for agricultural and horticultural use, and if necessary, (3) a formulation including a pesticide active ingredient at a specific ratio; a plant disease control agent obtained by mixing, and if necessary, formulating (1) the tetrazolyl oxime derivative or the like, (2) the fungicidal active ingredient for agricultural and horticultural use, and (3) a pesticide active ingredient at a specific ratio; a plant disease control agent obtained by adding (1) a formulation including the tetrazolyl oxime derivative or the like, (2) a formulation including the fungicidal active ingredient for agricultural and horticultural use, and if necessary, (3) a formulation including a pesticide active ingredient to water at a specific ratio.

The formulation may be a form that is able to be adopted according to the ordinary agricultural chemicals, for example, a wettable powder, granules, powder, emulsion, aqueous solution, suspension, flowable agent or the like.

The formulation is not particularly limited by the method or procedure thereof, and may be performed by well-known methods or procedures. In addition, various subsidiary materials useful for the formulation, such as carries, additives, solvents or the like are not particularly limited.

Examples of additives and/or carriers used for solid formulation include vegetable powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

For liquid formulations, oil fraction such as kerosene, xylene, solvent naphtha or the like; solvents such as cyclohexane, cyclohexanone, dimethylformamide, dimethylsulfoxide, alcohol, acetone, trichloroethylene, methyl isobutyl ketone, mineral oil, vegetable oil, water or the like may be used.

Moreover, a surfactant can be added to these formulations as necessary to obtain a uniform and stable form.

Examples of the surfactant include nonionic surfactants such as polyoxyethylene-alkyl phenyl ethers, polyoxyethylene-alkyl ethers, polyoxyethylene-higher fatty acid esters, polyoxyethylene-sorbitan fatty acid esters or polyoxyethylene-tristyryl phenyl ether, and sulfuric acid ester salts of polyoxyethylene-alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and isobutylene-maleic anhydrate copolymers.

The wettable powder, emulsion and towable agent obtained in this manner may be used in such a manner that the wettable powder, emulsion and flowable agent are diluted with water to a predetermined concentration and the resulting suspension or emulsion is sprayed on soil or mixed with soil before or after germination of weeds. The granules or powder may be directly sprayed on soil or mixed with soil before or after generation of weeds. The plant disease control agent of the present invention is generally applied in such a manner that the amount of the active ingredient is more than 0.1 g per hectare.

The plant disease control agent of the present invention provides superior fungicidal action against a wide range of types of fungi, such as fungi belonging to Oomycetes, Ascomycetes, Deuteromycetes or Basidiomycetes.

The plant disease control agent of the present invention can be used to control various plant diseases occurring during cultivation of agricultural and horticultural crops including flowering plants, lawn grasses and pasture grasses by seed treatment, foliar spraying, soil application or water surface application and the like.

Examples of the plant diseases which can be controlled by the plant disease control agent of the present invention include:

Sugar Beets:
Cercospora leaf spot (*Cercospora beticola*)
*Aphanomyces* root rot (*Aphanomyces cochlloides*)
Root rot (*Thanatephorus cucumeris*)
Leaf blight (*Thanatephorus cucumeris*)
Peanuts:
Brown leaf spot (*Mycosphaerella arachidis*)
Black leaf blight (*Mycosphaerella berkeleyi*)
Cucumbers:
Powdery mildew (*Sphaerotheca fuliginea*)
Downy mildew (*Pseudoperonospora cubensis*)
Gummy stem blight (*Mycosphaerella melonis*)
*Fusarium* wilt (*Fusarium oxysporum*)
Sclerotinia rot (*Sclerotinia sclerotiorum*)
Gray mold (*Botrytis cinerea*)
Anthracnose (*Colletotrichum obriculare*)
Scab (*Cladosporium cucumerinum*)
*Corynespora* leaf spot (*Corynespora cassicola*)
Damping-off (*Pythium debaryanum, Rhizoctonia solani* Kuhn)
Bacterial spot (*Pseudomonas syringae* pv. *Lecrymans*)
Tomatoes:
Gray mold (*Botrytis cinerea*)
Leaf mold (*Cladosporium fulvum*)
Late blight (*Phytophthora infestans*)
Eggplants:
Gray mold (*Botrytis cinerea*)
Black rot (*Corynespora melongenae*)
Powdery mildew (*Erysiphe cichoracearum*)
Leaf mold (*Mycovellosiella nattrassii*)
Strawberries:
Gray mold (*Botrytis cinerea*)
Powdery mildew (*Sphaerotheca humuli*)
Anthracnose (*Colletotrichurn acutatum, Colletotrichum fragariae*)
Phytophthora rot (*Phytophthora cactorum*)
Onions:
Neck rot (*Botrytis allii*)
Gray mold (*Botrytis cinerea*)
Leaf blight (*Botrytis squamosa*)
Downy mildew (*Peronospora destructor*)
Cabbage:
Clubroot (*Plasmodiophora brassicae*)
Bacterial soft rot (*Erwinia carotovora*)
Downy mildew (*Peronospora parasitica*)
Kidney beans:
Stem rot (*Sclerotinia sclerotiorum*)
Gray mold (*Botrytis cinerea*)
Apples:
Powdery mildew (*Podosphaera leucotricha*)
Scab (*Venturia inaequalis*)
Blossom blight (*Monilinia mali*)
Fruit spot (*Mycosphaerella pomi*)
*Valsa* canker (*Valsa mali*)
*Alternaria* blotch (*Alternaria mali*)
Rust (*Gymnosporangium yamadae*)
Ring rot (*Botryosphaeria berengeriana*)
Anthracnose (*Glomerella cingulata, Colletotrichum acutatum*)
Blotch (*Diplocarpon mali*)
Fly speck (*Zygophiala jamaicensis*)
Sooty blotch (*Gloeodes pomigena*)
Persimmons:
Powdery mildew (*Phyllactinia kakicola*)
Anthracnose (*Gloeosporium kaki*)
Angular leaf spot (*Cercospora kaki*)
Peaches:
Brown rot (*Monilinia fructicola*)
Scab (*Cladosporium carpophilum*)
*Phomopsis* rot (*Phomopsis* sp.)
Cherries:
Brown rot (*Monolinia fructicola*)
Grapes:
Gray mold (*Botrytis cinerea*)
Powdery mildew (*Uncinula necator*)
Ripe rot (*Glomerella cingulata, Colletotrichum acutatum*)
Downy mildew (*Plasmopara viticola*)
Anthracnose (*Elsinoe ampelina*)
Leaf blight (*Pseudocercospora vitis*)
Black rot (*Guignardia bidwellii*)
Pears:
Scab (*Venturia nashicola*)
Rust (*Gymnosporangium asiaticum*)
Black spot (*Alternaria kikuchiana*)
Ring rot (*Botryosphaeria berengeriana*)
Powdery mildew (*Phyllactinia mali*)
Tea:
Gray blight (*Pestalotia theae*)
Anthracnose (*Collectotrichum theae-sinensis*)
Citrus:
Scab (*Elsinoe fawcetti*)
Blue mold (*Penicillium italicum*)
Common green mold (*Penicillium digitatum*)
Gray mold (*Botrytis cinerea*)
Melanose (*Diaporthe citri*)
Canker (*Xanthomonas campestris* pv. *Citri*)
Wheat:
Powdery mildew (*Erysiphe graminis* f. sp. *tritici*)
*Fusarium* blight (*Gibberella zeae*)
Leaf rust (*Puccinia recondita*)
Browning root rot (*Pythium iwayamai*)
Snow mold (*Monographella nivalis*)

Eye spot (*Pseudocercosporella herpotrichoides*)
Speckled leaf blotch (*Septoria tritici*)
Glume blotch (*Leptosphaeria nodorum*)
*Typhula* snow blight (*Typhula incarnata*)
*Sclerotinia* snow blight (*Myriosclerotinia borealis*)
Take-all (*Gaeumanomyces graminis*)
Barley:
Stripe (*Pyrenophora graminea*)
Leaf blotch (*Rhynchosporium secalis*)
Loose smut (*Ustilago tritici, U. nuda*)
Rice:
Blast (*Pyricularia oryzae*)
Sheath blight (*Rhizoctonia solani*)
Bakanae disease (*Gibberella fujikuroi*)
Brown spot (*Cochliobolus niyabeanus*)
Seedling blight (*Pythium graminicolum*)
Bacterial leaf blight (*Xanthomonas oryzae*)
Bacterial seedling blight (*Burkholderia plantarii*)
Bacterial brown stripe (*Acidovorax avanae*)
Bacterial grain rot (*Burkholderia glumae*)
Tobacco:
*Sclerotinia* stem-rot (*Sclerotinia sclerotiorum*)
Powdery mildew (*Erysiphe cichoracearum*)
Tulips:
Gray mold (*Botrytis cinerea*)
Bent grass:
*Sclerotinia* snow blight (*Sclerotinia borealis*)
Bacterial shoot blight (*Pythium aphanidermatum*)
Orchard grass:
Powdery mildew (*Erysiphe graminis*)
Soybeans:
Purple stain (*Cercospora kikuchii*)
Downy mildew (*Peronospora Manshurica*)
*Phytophthora* root and stem rot (*Phytophthora sojae*)
Potatoes, tomatoes:
Late blight (*Phytophthora infestans*)

In addition, the plant disease control agent of the present invention has superior fungicidal effects against resistant organisms.

Examples of the resistant organism include gray mold (*Botrytis cinerea*), sugar beet *cercospora* leaf spot (*Cercospora beticola*), apple scab (*Venturia inaequalis*) and pear scab (*Venturia nashicola*), which exhibit resistance to benzimidazole fungicides such as thiophanate-methyl, benomyl and carbendazim; gray mold (*Botrytis cinerea*) which exhibits resistance to dicarboximide fungicides (for example, vinclozolin, procymidone, iprodione) and the like.

In addition, the plant disease control agent of the present invention causes little chemical damage, exhibits low toxicity to fish and warm-blooded animals, and has a high degree of safety.

EXAMPLES

The following provides a more detailed explanation of the present invention through examples. However, the present invention is not limited to the following examples.
(Chemical I)
10 parts of {6-([(Z)-(1-methyl-1H-5-tetrazolyl)phenyl methylene]aminooxymethyl)-2-pyridyl}carbamic acid t-butyl ester, 2 parts of polyoxyethylene aryl phenyl ether, 0.5 parts of dialkyl sulfosuccinate sodium salt, 5 parts of glycerin, 0.3 parts of xanthane gum and 82.2 parts of water were mixed and wet-milled until the grain size was reduced to 3 μm or less, thereby obtaining as Chemical I a suspension agent (SC agent) containing 10% of active ingredient.

In addition, {6-([(Z)-(1-methyl-1H-5-tetrazolyl)phenyl methylene]aminooxymethyl)-2-pyridyl}carbamic acid t-butyl ester is compound No. (3)-8 of Table 3, which was produced by the method described in WO 03/016303.
(Chemical II)

The following formulations (A) to (I) were prepared as Chemical II.

(A) Admire flowable (active ingredient: 20% of imidacloprid, manufactured by Bayer Holding Ltd.)

(B) Trifmine wettable powder (active ingredient: 30% of triflumizol, manufactured by Dow Chemical Japan Ltd.)

(C) Spinoace wettable granule (active ingredient: 25% of spinosad, manufactured by Dow Chemical Japan Ltd.)

(D) Tachigaren liquid formulation (active ingredient: 30% of hydroxyisoxazol, manufactured by Sankyo Agro Co., Ltd.)

(E) Topsin M wettable powder (active ingredient: 70% of thiophanate-methyl, manufactured by Nippon Soda Co., Ltd)

(F) Beam Sol (active ingredient: 20% of tricyclazoyl, manufactured by Sumitomo Chemical Company, Limited)

(G) Dantotsu water-soluble powder (active ingredient: 16% of clothiazine, manufactured by Sumitomo Chemical Company)

(H) Benreto wettable powder (active ingredient: 50% of benolyl, manufactured by Sumitomo Chemical Company)

(I) Mospiran SL liquid formulation (active ingredient: 18% of acetamiprid, manufactured by Nippon Soda Co., Ltd.)

Antifungal Plate Test of *Pythium graminicola*

Chemical I and Chemical II were added to water so as to adjust the concentration of the active ingredient to the concentrations shown in Table 1 or Table 2, thereby obtaining chemical solutions. The chemical solutions were added to a PDA culture media, and the concentration of the chemical solutions in the PDA culture media was adjusted to 1%, thereby obtaining agar plates. Mycelium disks (diameter of 4 mm) of *Pythium graminicola* were sown in the agar plates. The agar plates were statically placed for 3 to 4 days at 20° C., and the colony diameters were measured. Hyphal elongation inhibition rates relative to the control group are defined as prevent value and shown in Table 1 and Table 2. In addition, the expected values calculated using Colby's equation are shown in Table 1 and Table 2.

The hyphal elongation inhibition rate (%) was calculated using the following equation.

$$\text{Hyphal elongation inhibition rate}(\%) = (1-(\text{colony diameter in treatment group})/(\text{colony diameter in control group})) \times 100\%$$

The expected value was calculated using Colby's equation: $E=M+N-MN/100$. In the equation, E represents an expected prevent value (%), M represents a prevent value when using Chemical I alone (%), N represents a prevent value when using Chemical II alone (%).

In addition, in Table 1 and Table 2, Comparative Examples 1 and 12 show results when using a chemical solution including Chemical I alone, Comparative Examples 2 to 10 and 13 to 21 show results when using a chemical solution including Chemical II alone, and Comparative Examples 11 and 22 show results when using only water instead of a chemical solution.

TABLE 1

|  | Chemical I Concentration (ppm) | Chemical II Formulation | Chemical II Concentration (ppm) | Prevent Value (%) | Expected Value (%) |
|---|---|---|---|---|---|
| Example |  |  |  |  |  |
| 1 | 0.0025 | (A) | 100 | 93 | 68 |
| 2 |  |  | 10 | 94 | 68 |
| 3 |  |  | 1 | 93 | 68 |
| 4 |  | (C) | 10 | 93 | 68 |
| 5 |  |  | 1 | 93 | 68 |
| 6 |  | (D) | 10 | 93 | 68 |
| 7 |  | (I) | 100 | 93 | 68 |
| 8 |  |  | 10 | 91 | 68 |
| 9 |  |  | 1 | 90 | 68 |
| Comparative Example |  |  |  |  |  |
| 1 | 0.0025 | — | — | 68 | — |
| 2 | — | (A) | 100 | 0 | — |
| 3 |  |  | 10 | 0 | — |
| 4 |  |  | 1 | 0 | — |
| 5 |  | (C) | 10 | 0 | — |
| 6 |  |  | 1 | 0 | — |
| 7 |  | (D) | 10 | 0 | — |
| 8 |  | (I) | 100 | 0 | — |
| 9 |  |  | 10 | 0 | — |
| 10 |  |  | 1 | 0 | — |
| 11 |  | Control |  | 0 | — |

TABLE 2

|  | Chemical I Concentration (ppm) | Chemical II Formulation | Chemical II Concentration (ppm) | Prevent Value (%) | Expected Value (%) |
|---|---|---|---|---|---|
| Example |  |  |  |  |  |
| 10 | 0.0025 | (B) | 10 | 90 | 70 |
| 11 |  | (E) | 10 | 90 | 70 |
| 12 |  | (F) | 10 | 96 | 70 |
| 13 |  |  | 1 | 92 | 70 |
| 14 |  | (G) | 100 | 97 | 70 |
| 15 |  |  | 10 | 94 | 70 |
| 16 |  |  | 1 | 91 | 70 |
| 17 |  | (H) | 100 | 99 | 76 |
| 18 |  |  | 1 | 92 | 70 |
| Comparative Example |  |  |  |  |  |
| 12 | 0.0025 | — | — | 70 | — |
| 13 | — | (B) | 10 | 0 | — |
| 14 |  | (E) | 10 | 0 | — |
| 15 |  | (F) | 10 | 0 | — |
| 16 |  |  | 1 | 0 | — |
| 17 |  | (G) | 100 | 0 | — |
| 18 |  |  | 10 | 0 | — |
| 19 |  |  | 1 | 0 | — |
| 20 |  | (H) | 100 | 22 | — |
| 21 |  |  | 1 | 0 | — |
| 22 |  | Control |  | 0 | — |

As shown in Table 1 and Table 2, the prevent values when using a chemical solution including both Chemical I and Chemical II were higher than the expected prevent values calculated by substituting the prevent values when using a chemical solution including Chemical I or Chemical II alone into Colby's equation. Therefore, it is apparent that synergetic effects can be obtained by using Chemical I together with Chemical II.

INDUSTRIAL APPLICABILITY

The plant disease control agent of the present invention demonstrates excellent control effects against plant disease at low doses, and eliminates concern over chemical damage to useful plants, thereby making it extremely useful in the industrial field.

The invention claimed is:

1. A plant disease control agent comprising:
A. {6-([(Z)-(1-methyl-1H-5-tetrazolyl)phenylmethylene]aminooxymethyl)-2-pyridyl}carbamic acid t-butyl ester (compound 3-8), and at least one selected from the group consisting of triflumizole and salts thereof as the only active ingredients; or
B. {6-([(Z)-(1-methyl-1H-5-tetrazolyl)phenylmethylene]aminooxymethyl)-2-pyridyl}carbamic acid t-butyl ester (compound 3-8), and at least one selected from the group consisting of hydroxy isoxazole and salts thereof as the only active ingredients.

2. The plant disease control agent of claim 1, wherein the plant disease control agent comprises 6-([[(Z)-(1-methyl-1H-5-tetrazolyl)phenylmethylene]aminooxymethyl)-2-pyridyl}carbamic acid t-butyl ester and at least one selected from the group consisting of triflumizole and salts thereof as the only active ingredients.

3. The plant disease control agent of claim 1, wherein the plant disease control agent comprises {6-([[(Z)-(1-methyl-1H-5-tetrazolyl)phenylmethylene]aminooxymethyl)-2-pyridyl}carbamic acid t-butyl ester and at least one selected from the group consisting of a hydroxy isoxazole and salts thereof as the only active ingredients.

4. A plant disease control agent consisting of:
   {6-([[(Z)-(1-methyl-1H-5-tetrazolyl)phenylmethylene]aminooxymethyl)-2-pyridyl}carbamic acid t-butyl ester;
   at least one selected from the group consisting of triflumizole and salts thereof; and
   at least one selected from the group consisting of a carrier, an additive and a solvent.

5. A plant disease control agent consisting of:
   {6-([[(Z)-(1-methyl-1H-5-tetrazolyl)phenylmethylene]aminooxymethyl)-2-pyridyl}carbamic acid t-butyl ester;
   at least one selected from the group consisting of hydroxy isoxazole and salts thereof; and
   at least one selected from the group consisting of a carrier, an additive and a solvent.

* * * * *